United States Patent [19]

Sauer et al.

[11] Patent Number: 4,740,509
[45] Date of Patent: Apr. 26, 1988

[54] 12- AND 13-BROMOERGOLINES USEFUL FOR TREATING HYPERTENSION

[75] Inventors: Gerhard Sauer; Josef Heindl; Gertrud Schroeder; Helmut Wachtel, all of Berlin, Fed. Rep. of Germany

[73] Assignee: Schering Aktiengesellschaft, Berlin and Bergkamen, Fed. Rep. of Germany

[21] Appl. No.: 909,837

[22] Filed: Sep. 19, 1986

[30] Foreign Application Priority Data

Sep. 19, 1985 [DE] Fed. Rep. of Germany ....... 3533675

[51] Int. Cl.⁴ ..................... A61K 457/12; C07D 31/48
[52] U.S. Cl. ........................................ 514/288; 546/68
[58] Field of Search ............................ 546/68, 67, 69; 514/288

[56] References Cited

U.S. PATENT DOCUMENTS 3,904,634  9/1975  Arcari et al. ........................ 546/67
3,953,454  4/1976  Zikán et al. ........................ 546/68

FOREIGN PATENT DOCUMENTS

| | | |
|---|---|---|
| EP-A 0021206 | 7/1980 | European Pat. Off. . |
| 048695 | 3/1982 | European Pat. Off. . |
| 056358 | 7/1982 | European Pat. Off. . |
| EP-A 0082808 | 6/1983 | European Pat. Off. . |
| 118848 | 9/1984 | European Pat. off. ............... 546/68 |
| EP-A 0160842 | 11/1985 | European Pat. Off. . |
| 330912 | 5/1978 | Fed. Rep. of Germany . |
| 2924102 | 12/1980 | Fed. Rep. of Germany ........ 546/68 |
| 3001752 | 7/1981 | Fed. Rep. of Germany ........ 546/68 |
| 309493 | 9/1984 | Fed. Rep. of Germany . |
| 3413657 | 10/1985 | Fed. Rep. of Germany ........ 546/68 |
| 445784 | 6/1986 | Fed. Rep. of Germany . |
| 584220 | 1/1977 | Switzerland . |

OTHER PUBLICATIONS

Bernardi et al. Il. Farmco Ed. Sci. 1975, pp. 789–801.
Gull, CA 98-34829r.
Berde et al. Ergot Alkaloids and Related Compounds, pp. 60–61.

*Primary Examiner*—Donald G. Daus
*Assistant Examiner*—Cecilia Shen
*Attorney, Agent, or Firm*—Millen & White

[57] ABSTRACT

Novel 12- and 13-bromoergoine derivatives are suitable as medicines for treating psychic disorders of the depressive array of symptoms and also as intermediates.

16 Claims, No Drawings

12- AND 13-BROMOERGOLINES USEFUL FOR TREATING HYPERTENSION

BACKGROUND OF THE INVENTION

This invention relates to 12- and 13-bromoergoline derivatives, a process for their preparation, and their use as medicines or as intermediates.

SUMMARY OF THE INVENTION

It is an object of this invention to provide new compounds having valuable properties as medicaments or as intermediates.

Upon further study of the specification and appended claims, further objects and advantages of this invention will become apparent to those skilled in the art.

These objects have been achieved by providing 12- and 13-bromoergoline derivatives of this invention having the Formula I

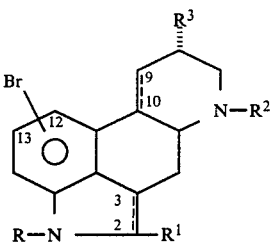

wherein
R is hydrogen or acyl,
$R^1$ is hydrogen or bromine, or alkylthio, wherein R and $R^1$ cannot be simultaneously a substituent from the group of acyl, bromine and alkylthio, i.e., at least one of R and $R^1$ is H,
$R^2$ is a lower alkyl group,
$R^3$ is an NH—CO—NEt$_2$-group or an NH—C—S—NEt$_2$-group, and
$C_9$=$C_{10}$ and $C_2$=$C_3$ independently are each a CC-single or a C=C-double bond, and
the hydrogen atom in the 10-position is in the α-configuration if $C_9$=$C_{10}$ is a CC-single bond, and the hydrogen atom in the 3-position is in the α-configuration or β-configuration if $C_2$=$C_3$ is a CC-single bond, and
$R^1$ is hydrogen if Br is in the 12-position, and $C_2$=$C_3$ is a C=C double bond if R1 is bromine.
and their acid addition salts.

Lower alkyl groups include those of up to 4 carbon atoms, for example methyl, ethyl, n-propyl, isopropyl, n-butyl, isobutyl and tert-butyl. The alkyl mercaptan and acyl blocking groups (e.g., alkanoyl) and R and $R^1$ are derived from hydrocarbon residues of up to 2 carbon atoms, the acetyl and methylmercaptan groups being preferred. Contemplated equivalents of these groups include those of higher carbon atoms.

The salts of the compounds of this invention according to Formula I are acid addition salts and are derived from conventionally employed acids. Such acids are, for example, inorganic acids, such as, for example, hydrochloric acid, nitric acid, phosphoric acid, sulfuric acid, hydrobromic acid, hydriodic acid, nitrous acid or phosphorus acid, or organic acids, such as, for example, aliphatic mono- or dicarboxylic acids, phenyl-substituted alkanecarboxylic acids, hydroxyalkanecarboxylic acids or alkenedicarboxylic acids, aromatic acids or aliphatic or aromatic sulfonic acids. Physiologically acceptable salts of these acids are, therefore, e.g., the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate or naphthalene-2-sulfonate.

As compared with conventional ergolines not brominated in the 12- or 13-position, such as, for example, terguride, the compounds of this invention exhibit a central $\alpha_2$-receptor-blocking activity which is stronger or at least equally strong, with a weaker or a lack of antidopaminergic effects. This profile of activity renders the compound valuable substances of the treatment of psychic disorders of the depressive array of symptoms.

Thus the compounds can be used as general antidepressants to treat symptoms including endogenous depression, agitated or restrained depression, idiopathic depression, lack or loss of drive, of interest, of thinking, of energy, of hope, etc., or a feeling of emptiness. They also are useful to treat excitability, subjective feelings of unrest, dysphoria or anxiety.

the antidepressive effect of the compounds of this invention is based on central $\alpha_2$-receptor blockage causing increased release of noradrenalin in the brain and moreover showing the antidepressive activity as a consequence thereof. Central $\alpha_2$-receptor blockage was demonstrated in an interaction test with the $\alpha_2$-receptor agonist clonidine in mice after a single i.p. pretreatment (parameter: relief of hypothermia caused by clonidine 0.1 mg/kg i.p.). Male NMRI mic were pretreated with various doses of 1,1-diethyl-(6-methyl-8α-ergolinyl-)urea (TDHL) or with 12- or 13-brominated ergolinylureas which per se do not affect thermoregulation of the test animals, or with carrier medium. Thirty minutes later, all animals received clonidine 0.1 mg/kg i.p. Rectal temperature was measured with the aid of a thermal probe 60 minutes after the test compound or the carrier medium (=30 minutes after clonidine). While the mice pretreated with carrier medium showed hypothermia, the effect of clonidine of lowering body temperature was cancelled out in dependence on the dose in animals pretreated with TDHL or 12- or 13-bromoergolinylureas. As can be seen from Table 1, the clonidine-antagonistic effect was statistically significant after 13-Br-TDHL in a dosage of 0.39 mg/kg and after 13-Br-2,3-dihydro-TDHL as well as TDHL in a dosage of 1.56 mg/kg.

Central dopamine receptor blockage was demonstrated in an interaction test with the dopamine receptor agonist apomorphine in mice after a single i.p. pretreatment. (Parameter: relief of hypothermia caused by apomorphine 5 mg/kg i.p.) The further procedure was like the method set forth in connection with central $\alpha_2$-receptor blockage.

As can be seen from Table 2, the apomorphine antagonistic activity was highly significant statistically after TDHL in a dosage of 3.13 mg/kg. After 13-Br-TDHL was administered in a dosage of 1.56 mg/kg, the effect was statistically significant, but was weaker quantitatively.

Based on these findings, the compounds of this invention can thus be utilized as adjunct to neuroleptics for the treatment of psychosis of the schizophrenic array of symptoms especially with negative clinical symptoms or as antidepressants. Furthermore, the compounds of this invention show blood-pressure lowering effect and therefore are useful as medicines for the therapy of hypertension.

in compounds of general Formula I having a $C_2$–$C_3$-single bond, splitting off an acyl group and, if desired, dehydrogenating to the $C_2$=$C_3$-double bond, and thereafter optionally converting the urea into the thiourea and, if desired, forming the acid addition salt.

The bromination is conducted in an inert solvent, such as, for example, chlorinated hydrocarbons, e.g., chloroform, methylene chloride or protonic solvents, such as aqueous acetic acid, glacial acetic acid, or ethers, such as tetrahydrofuran, dioxane, diisopropyl ether, etc., in a temperature range from $-20°$ C. to $80°$ C., preferably at room temperature. Suitable brominating agents include elemental bromine or bromination reagents, such as pyridine hydrobromide perbromide,

TABLE 1

Antagonistic Effect on Hypothermia in Mice Caused by Clonidine (0.1 mg/kg i.p.) of Pretreatment (30 min. i.p.) with Various Doses of 13-Brominated Ergolinylureas. Rectal Temperature of the Test Animals Was Measured 30 min. after Clonidine (= 60 min. after Test Compound) (x: $p < 0.05$, xx: $p < 0.01$ vs. Control; Variance Analysis/Dunnett Test)

| Compound | n | Rectal Temperature [°C.] (Average Value ± S.E.M.) Test Compound Dose [mg/kg] | | | | | | | |
|---|---|---|---|---|---|---|---|---|---|
| | | Control | 0.05 | 0.1 | 0.2 | 0.39 | 0.78 | 1.56 | 3.13 |
| TDHL. | 8 | 33.1 ± 0.2 | — | — | — | 33.6 ± 0.2 | 33.7 ± 0.3 | 34.1 ± 0.2 xx | 34.7 ± 0.3 xx |
| 13-Br—TDHL | 8 | 33.2 ± 0.3 | 33.7 ± 0.2 | 32.9 ± 0.2 | 33.8 ± 0.1 | 34.2 ± 0.3 x | 34.5 ± 0.3 xx | 36.1 ± 0.2 xx | — |
| 13-Br—2,3-dihydro-TDHL | 8 | 34.1 ± 0.2 | — | — | — | 34.3 ± 0.2 | 34.5 ± 0.2 | 36.0 ± 0.4 xx | 36.4 ± 0.4 xx |

TABLE 2

Antagonistic Effect on Hypothermia in Mice Caused by Apomorphine (5 mg/kg i.p.) of Pretreatment (30 min. i.p.) with Various Doses of 13-Bromoergolinylureas. Rectal Temperature of the Test Animals Was Measured 30 min. after Apomorphine (= 60 min. after Test Compound) (x: $p < 0.05$, xx: $p < 0.01$ vs. Control; Variance Analysis/Dunnett Test)

| Compound | n | Rectal Temperature [°C.] (Average Value ± S.E.M.) Test Compound Dose [mg/kg] | | | | | | | | |
|---|---|---|---|---|---|---|---|---|---|---|
| | | Control | 0.05 | 0.1 | 0.2 | 0.39 | 0.78 | 1.56 | 3.13 | 6.25 |
| TDHL | 8 | 32.5 ± 0.4 | — | — | — | — | 33.9 ± 0.5 | 33.8 ± 0.4 | 35.1 ± 0.5 xx | 35.5 ± 0 |
| 13-Br—TDHL | 8 | 32.6 ± 0.2 | 32.5 ± 0.2 | 32.2 ± 0.2 | 32.6 ± 0.4 | 33.0 ± 0.3 | 33.3 ± 0.2 | 33.5 ± 0.3 x | — | |

The compounds of this invention can be prepared in accordance with conventional methods. For example, the comounds of Formula I can be obtained by reacting a compound of Formula II

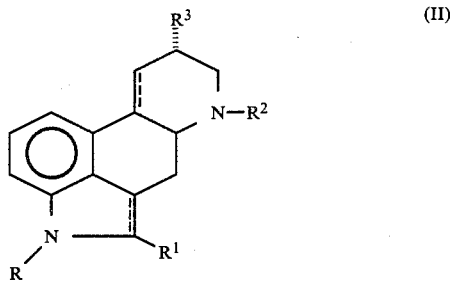

(II)

wherein
R, $R^2$, $R^3$ and C==C have the meanings given above and $R^1$ is hydrogen or an alkylthio group, with a brominating agent.

Subsequently, if desired, there can follow in compounds of general Formula I having a $C_2$=$C_3$-double bond, splitting off 2-bromine or an alkylthio group and optionally hydrogenating the $C_2$=$C_3$-double bond, or, pyrrolidone hydroperbromide, and others.

The alkylthis group is split off, for example, by performing the reaction with a reducing agent, such as sodium borohydride in trifluoroacetic acid at a reaction temperature of $-40°$ C. to $+20°$ C., and optionally dissolving the reaction product in an inert solvent, e.g., alcohols, such as methanol, ethanol, or ethers, such as dioxane and tetrahydrofuran, and subsequently combining the solution with a base, such as, for example, aqueous alkali hydroxide solution, e.g., aqueous potassium and sodium hydroxide solution, or alkali alcoholates, such as sodium ethylate and sodium methylate.

By enlarging the amount of sodium borohydride employed (about 2-molar) and lengthening the reaction period to about 5 hours, the $C_2$=$C_3$-double bond is hydrogenated at the same time, with splitting off of the mercaptan group.

Splitting off bromine in the 2-position is suitably carried out with sodium borohydride and a cobalt salt, e.g., cobalt chloride or cobalt sulfate in protonic solvents, such as, for example, alcohols, such as methanol, ethanol, isopropanol, water, or mixtures thereof, at temperatures of $-20°$ C. to $+50°$ C.

The acyl residue is split off in an inert solvent, such as, for example, chlorinated hydrocarbons, alcohols, ethers, water, and other materials, at temperatures of between 0° C. and 100° C., with the use of inorganic and organic based, such as KOH, NaOH, hydrazine, Na methylate, K tert-butylate, etc.

The splitting off step can also be performed in the presence of acids, preferably inorganic acids, such as, for example, HCl, H$_2$SO$_4$, etc.

The introduction of the C$_2$=C$_3$-double bond can take place according to methods known per se, such as, for example, by dehydrogenation with MnO$_2$ (DOS No. 3,309,493) or tert-butyl hypochlorite (DOS No. 3,445,784.4).

The 8$\alpha$-urea derivatives can be converted into the corresponding thiourea derivatives by reaction with phosphorus oxychloride and a thiolating agent in accordance with German Patent Application No. P 35 28 576.1.

When bromine is in the 12-position only compounds with R$^1$ in the meaning of hydrogen could be isolated and when R$^1$ is bromine the C$_2$==C$_3$ single bond split of HBr.

All of the reactions are customarily performed under an inert gas atmosphere, such as, for example, argon or nitrogen.

For the formation of salts, the compounds of general Formula I can be dissolved in a small amount of methanol or methylene chloride and combined with a concentrated solution of the corresponding acid in methanol at room temperature.

The starting materials of Formula II are all known and/or readily preparable from known starting materials using conventional reactions for example in accordance with Nos. EP-A160842 and EP-A118848.

For using the compounds of this invention as medicinal agents, they can be brought into the form of a pharmaceutical preparation containing, besides the active agent, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be present in solid form, e.g., as tablets, dragees, suppositories, capsules, or in the liquid form, for example as solutions, suspensions or emulsions. Optionally, they contain moreover auxiliary materials, such as preservatives, stabilizers, wetting agents, or emulsifiers, salts for altering osmotic pressure, or buffers.

The pharmacologically active compounds of this invention can be processed in accordance with conventional methods of galenic pharmacy to produce medicinal agents for administration to patients, e.g., mammals including humans, as antidepressants.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

Generally, the compounds of this invention are dispensed in unit dosage form comprising 0.1 to 10 mg in a pharmaceutically acceptable carrier per unit dosage. They are incorporated in topical formulations in concentrations of about 1 to 10 weight percent.

The dosage of the compounds according to this invention generally is 0.001 to 1 mg/kg/day, preferably 0.01 to 0.1 when administered to patients, e.g., humans to treat depression analogously to the known agent Idazoxan (BP No. 2068376).

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The novel 12- and 13-bromoergolines of this invention can also be utilized as intermediates for the production of novel pharmacologically active ergoline derivatives. The latter include those of copending Ser. No. 909,838 filed on even date and corresponding to No. DE-OS-35 33672 of Sept. 19, 1985, all of which disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

3-(13-Bromo-6-methyl-2-methylthio-8$\alpha$-ergolinyl)-1,1-diethylurea

A solution is prepared from 11.2 g of 3-(6-methyl-2-methylthio-8$\alpha$-ergolinyl)-1,1-diethylurea (29 mmol) in 400 ml of methylene chloride p.a. and, at room temperature, 1.45 ml of bromine (26 mmol) dissolved in 100 ml of methylene chloride p.a. is added dropwise thereto within 20 minutes. After 15 minutes of agitation, the solvent is distilled off under vacuum, the residue is taken up in methylene chloride and methanol, and crystallized by adding ethyl acetate with a small amount of diisopropyl ether and by removing the readily volatile solvents by distillation.

Yield: 12.6 g (93% of theory).

[$\alpha$]$_D$ = −2° (0.5% in methanol).

EXAMPLE 2

3-(13-Bromo-6-methyl-8$\alpha$-ergolinyl)-1,1-diethylurea

Under argon, 10.74 g (23 mmol) of 3-(13-bromo-6-methyl-2-methylthio-8$\alpha$-ergolinyl)-1,1-diethylurea is dissolved in 200 ml of trifluoroacetic acid. At a temperature of −15° C., sodium borohydride tablets are added thereto in 8 portions of 0.5 g each. After a reaction period of 1½ hours at −15° C., the mixture is poured on 500 ml of ice, the solution is gently rendered alkaline with 25% strength ammonia solution, and extracted with methylene chloride. The organic phases are dried over magnesium sulfate and evaporated. The crude product is dissolved under argon in 100 ml of methanol p.a. and combined with 50 ml of 7N potassium hydroxide solution. The mixture is stirred for 2 hours at room temperature until the reaction is completed; then the mixture is poured on 150 ml of ice to work it up, and extracted with methylene chloride. The organic phases are washed with water and dried over magnesium sulfate. The concentrated crude product is chromatographed on 1.4 kg of silica gel with methylene chloride/methanol in a ratio of 97:3. In this way, 6.0 g is isolated which is crystallized from ethyl acetate/diisopropyl ether to complete the purification process, thus obtaining 5.44 g of 3-(13-bromo-6-methyl-8α-ergolinyl)-1,1-diethylurea (56% yield).

$[\alpha]_D = -9.6°$ (0.5% in $CH_3OH$).
$[\alpha]_D = -6.4°$ (0.5% in $CH_3OH$/pyridine).

EXAMPLE 3

3-(13-Bromo-6-n-propyl-8α-ergolinyl)-1,1-diethylurea

Analogously to Example 1 and Example 2, 3-(2-methylthio-6-n-propyl-8α-ergolinyl)-1,1-diethylurea yields 3-(13-bromo-6-n-propyl-8α-ergolinyl)-1,1-diethylurea in a 42% yield.

EXAMPLE 4

3-(13-Bromo-2,3-dihydro-6-methyl-8α-ergolinyl)-1,1-diethylurea

Analogously to Example 2-(13-bromo-6-methyl-2-methylthio-8α-ergolinyl)-1,1-diethylurea can be used to produce, by doubling the amount of sodium borohydride and lengthening the reaction period to 5 hours, 3-(13-bromo-2,3-dihydro-6-methyl-8α-ergolinyl)-1,1-diethylurea in a chromatographic yield of 52%. The compound is crystallized from ethyl acetate.

$[\alpha]_D = -19°$ (0.5% in chloroform).

EXAMPLE 5

3-(13-Bromo-6-methyl-8α-ergolinyl)-1,1-diethylurea 10 g of 1,1-diethyl-3-(6-methyl-8α-ergolinyl)urea (terguride) (30 mmol) is dissolved in 550 ml of methylene chloride and, under ice cooling, 8.8 ml of 33% strength solution of hydrogen bromide in glacial acetic acid is added thereto. With continued cooling, a solution of 3.1 ml of bromine (60 mmol) in 400 ml of methylene chloride is added dropwise thereto within 30 minutes. The crystalline slurry is combined with 200 ml of diisopropyl ether, and the crystals are filtered off after stirring for 20 minutes. Recrystallization from methylene chloride, methanol and diisopropyl ether yields 10.5 g of 3-(2,13-dibromo-6-methyl-8α-ergolinyl)-1,1-diethylurea (71% of theory).

$[\alpha]_D = +1°$ (0.3% in methanol).

5.25 g of this compound (10.5 mmol) is dissolved in 2.1 l of methanol; the solution is cooled to −20° C. and combined with 15.7 g of cobalt chloride ($6H_2O$). Then, under continued cooling, 3 g of sodium borohydride in tablet form is added thereto and the mixture is stirred for one hour. The reaction solution is introduced into about 3 l of ice, neutralized with 25% strength ammonia solution (0.5 liter) and extracted with methylene chloride. The organic phase is dried with sodium sulfate and evaporated. The crude product yields, after crystallization from ethyl acetate and diisopropyl ether, 3.5 g of 3-(13-bromo-6-methyl-8α-ergolinyl)-1,1-diethylurea (79% of theory).

$[\alpha]_D = -9°$ (0.5% in methanol).

EXAMPLE 6

3-(1-Acetyl-12-bromo-2,3-dihydro-6-methyl-8α-ergolinyl)-1,1-diethylurea

A solution of 5 g of 3-(1-acetyl-2,3-dihydro-6-methyl-8α-ergolinyl)-1,1-diethylurea in 25 ml of 5% acetic acid is combined with 1.0 ml of bromine, and the mixture is agitated for 35 hours at room temperature. The reaction mixture is poured on 100 ml of ice, combined with 25% strength ammonia solution until alkaline reaction occurs, and extracted with dichloromethane.

The combined organic phases are dried over magnesium sulfate and concentrated, thus obtaining 5.4 g of 3-(1-acetyl-12-bromo-2,3-dihydro-6-methyl-8α-ergolinyl)-1,1-diethylurea as a mixture of diastereomers which is separated by chromatography on silica gel with dichloromethane/ethanol in a proportion of 95:5. A fraction 1 is isolated in an amount of 1.6 g, and, as fraction 2, 1.5 g, which are crystallized from ethyl acetate/diisopropyl ether to complete the purification. Yield: 0.9 g of 3-(1-acetyl-12-bromo-2,3α-dihydro-6-methyl-8α-ergolinyl)-1,1-diethylurea (fraction 1), $[\alpha]_D = -16°$ (0.5% in chloroform), and 0.8 g of 3-(1-acetyl-12-bromo-2,3β-dihydro-6-methyl-8α-ergolinyl)-1,1-diethylurea (fraction 2), $[\alpha]_D = +28.4°$ (0.5% in chloroform).

EXAMPLE 7

3-(12-Bromo-2,3α-dihydro-6-methyl-8α-ergolinyl)-1,1-diethylurea

A solution of 1.8 g of 3-(1-acetyl-12-bromo-2,3α-dihydro-6-methyl-8α-ergolinyl)-1,1-diethylurea in 50 ml of 1N hydrochloric acid is stirred for 4 hours at 70°-80° C. The reaction mixture is poured on 100 ml of ice, combined with 25% strength ammonia solution until the reaction is alkaline, and extracted with dichloromethane. The combined organic phases are dried over magnesium sulfate, concentrated, and the residue chromatographed on silica gel with dichloromethane/methanol in a ratio of 97:3, thus isolating 300 mg of an oily product which, for complete purification, is crystallized from ethyl acetate/diisopropyl ether. Yield: 200 mg of 3-(12-bromo-2,3α-dihydro-6-methyl-8α-ergolinyl)-1,1-diethylurea.

$[\alpha]_D = -6.5°$ (0.5% in chloroform).

EXAMPLE 8

3-(12-Bromo-2,3β-dihydro-6-methyl-8α-ergolinyl)-1,1-diethylurea

Analogously to Example 7, 900 mg of 3-(1-acetyl-12-bromo-2,3β-dihydro-6-methyl-8α-ergolinyl)-1,1-diethylurea yields 500 mg of an oily product which, to complete purification, is crystallized from toluene/pentane, thus obtaining 240 mg of 3-(12-bromo-2,3β-dihydro-6-methyl-8α-ergolinyl)-1,1-diethylurea.

$[\alpha]_D = +50°$ (0.5% in chloroform).

EXAMPLE 9

3-(12-Bromo-6-methyl-8α-ergolinyl)-1,1-diethylurea

A solution of 4.2 g of 3-(12-bromo-2,3-dihydro-6-methyl-8α-ergolinyl)-1,1-diethylurea in a mixture of 300 ml of absolute tetrahydrofuran and 50 ml of absolute triethylamine is combined at −40° C. with a solution of 1.58 ml of tert-butyl hypochlorite in 250 ml of absolute tetrahydrofuran, and the mixture is stirred for 15 minutes at −40° C. The reaction mixture is poured on 1 liter of ice, combined with 25% strength ammonia solution until the reaction is alkaline, and extracted with dichloromethane. The combined organic phases are dried over magnesium sulfate and concentrated. The crude product is crystallized from ethyl acetate/pentane, thus obtaining 3 g of 3-(12-bromo-6-methyl-8α-ergolinyl)-1,1-diethylurea.

$[\alpha]_D = -0.3°$ (0.5% in chloroform).

EXAMPLE 10

3-(1-Acetyl-12-bromo-9,10-didehydro-6-methyl-8α-ergolinyl)-1,1-diethylurea

The compound is produced by reacting 3-(1-acetyl-9,10-didehydro-2,3-dihydro-6-methyl-8α-ergolinyl)-1,1-diethylurea with elemental bromine in 5% acetic acid, analogously to Example 6.

EXAMPLE 11

3-(12-Bromo-9,10-didehydro-2,3β-dihydro-6-methyl-8α-ergolinyl)-1,1-diethylurea

This compound is obtained—analogously to Example 7—from 3-(1-acetyl-12-bromo-9,10-didehydro-2,3-dihydro-6-methyl-8α-ergolinyl)-1,1-diethylurea by heating with 1N hydrochloric acid.

EXAMPLE 12

3-(12-Bromo-9,10-didehydro-6-methyl-8α-ergolinyl)-1,1-diethylurea

This compound is prepared analogously to Example 9 by reacting 3-(12-bromo-9,10-didehydro-2,3-dihydro-6-methyl-8α-ergolinyl)-1,1-diethylurea with tert-butyl hypochlorite in the presence of triethylamine.

EXAMPLE 13

3-(12-Bromo-6-methyl-8α-ergolinyl)-1,1-diethylthiourea

At −20° C., 6.29 g of 3-(12-bromo-6-methyl-8α-ergolinyl)-1,1-diethylurea (15 mmol) is dissolved in a mixture of 4.13 g of freshly distilled phosphorus oxychloride (45 mmol) and 50 ml of anhydrous methylene chloride, and the temperature is allowed to rise to +10° C. within 4 hours. The mixture is agitated overnight at room temperature, then for another 2 hours at 40° C., and subsequently the solvent is distilled off under vacuum. The residue is dissolved in 50 ml of anhydrous acetonitrile, cooled to −10° C., combined with 7.2 g of potassium ethylxanthate (45 mmol) and stirred for 20 hours at room temperature. The solvent is extensively distilled off, then the mixture is divided between ethyl acetate and saturated sodium carbonate solution, the organic phase is dried with sodium sulfate, and evaporated. The residue is crystallized from ethyl acetate, thus obtaining 5.03 g (77%) of 3-(12-bromo-6-methyl-8α-ergolinyl)-1,1-diethylthiourea.

$[\alpha]_D = +55°$ (0.5% in chloroform).

EXAMPLE 14

3-(13-Bromo-6-methyl-8α-ergolinyl)-1,1-diethylthiourea

Analogously to Example 13, 6.29 of 3-(13-bromo-6-methyl-8α-ergolinyl)-1,1-diethylurea is reacted, worked up, and yields 4.9 g (75%) of 3-(13-bromo-6-methyl-8α-ergolinyl)-1,1-diethylthiourea.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 12- or 13-bromoergoline of the formula

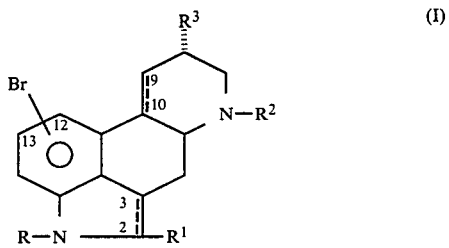

wherein

R is hydrogen of $C_{1-2}$-alkanoyl, $R^1$ is hydrogen, bromine, or $C_{1-2}$-alkylthio, wherein at least one of R and $R^1$ is H, and when Br is in the 12-position, $R^1$ is H, and when $R^1$ is bromine $C_2=C_3$ is a double bond, $R^2$ is lower alkyl, $R^3$ is NH—CO—NEt$_2$ or NH—CS—NEt$_2$, $C_9=C_{10}$ and $C_2=C_3$ each independent is a CC-single or a C=C-double bond, and the hydrogen atom in the 10-position is in the α-configuration if $C_9=C_{10}$ is a CC-single bond, and the hydrogen atom in the 3-position is in the α-configuration or β-configuration if $C_2=C_3$ is a CC-single bond, or a pharmaceutically acceptable acid addition salt thereof.

2. A compound of claim 1 wherein Br is in the 12-position.

3. A compound of claim 1 wherein Br is in the 13-position.

4. A compound of claim 1 wherein $R^1$ is Br.

5. A compound of claim 1 wherein $R^1$ is H.

6. A compound of claim 1 wherein $R^1$ is alkylthio.

7. A compound of claim 1 wherein $R^3$ is NH—CO—NEt$_2$.

8. A compound of claim 1 wherein $R^1$ is NH—CS—NEt$_2$.

9. A compound of claim 1 wherein $C_9=C_{10}$ is a single bond.

10. A compound of claim 1 wherein $C_9=C_{10}$ is a double bond.

11. 3-(1-acetyl-12-bromo-2,3-dihydro-6-methyl-8α-ergolinyl)-1,1-diethylurea, 3-(1-acetyl-12-bromo-9,10-didehydro-6-methyl-8α-ergolinyl)-1,1-diethylurea, 3-(13-Bromo-6-methyl-2-methylthio-8α-ergolinyl)-1,1-diethylurea, 3-(13-bromo-6-methyl-8α-ergolinyl)-1,1-diethylurea, 3-(13-bromo-6n-propyl-8α-ergolinyl)-1,1-diethylurea, 3-(13-bromo-2,3-dihydro-6-methyl-8α-ergolinyl)-1,1-diethylurea, 3-(2,13-dibromo-6-methyl-8α-ergolinyl)-1,1-diethylurea, 3-(12-bromo-2,3α-dihydro-6-methyl-8α-ergolinyl)-1,1-diethylurea, 3-(12-bromo-2,3β-dihydro-6-methyl-8α-ergolinyl)-1,1-diethylurea, 3-(12-bromo-6-methyl-8α-ergolinyl)-1,1-diethylurea, 3-(12-bromo-9,10-didehydro-2,3β-dihydro-6-methyl-8α-ergolinyl)-1,1-diethylurea, 3-(12-bromo-9,10-didehydro-6-methyl-8α-ergolinyl)-1,1-diethylurea, 3-(12-bromo-6-methyl-8α-ergolinyl)-1,1-diethylthiourea, or 3-(13-bromo-6-methyl-8α-ergolinyl)-1,1-diethylthiourea, each a compound of claim 1.

12. A pharmaceutical composition comprising a compound of claim 1 and a pharmaceutically acceptable carrier.

13. A composition of claim 12 wherein the amount of said compound is 0.1–10 mg.

14. A method of treating hypertension comprising administering a compound of claim 1.

15. A method of claim 14, wherein said compound is administered at a dosage of 0.001–1 mg/kg/day.

16. A method of claim 14, wherein said compound is administered at a dosage of 0.01–0.1 mg/kg/day.

* * * * *